United States Patent
Heltovics et al.

(10) Patent No.: US 7,208,465 B2
(45) Date of Patent: Apr. 24, 2007

(54) METHODS AND COMPOSITIONS FOR IMPROVED FRAGRANCING OF A SURFACE

(75) Inventors: Gabor Heltovics, Budapest (HU); Lynette Anne Makins Holland, Watford (GB); Jane Margaret Warwick, Willerby (GB); Delyth Myfanwy Jenkins, Egham (GB); Karen Lorraine Sutton, Canberley (GB); Emma Louise Pretswell, Bracknell (GB); Andrew James Peter Shefferd, Slough (GB)

(73) Assignee: The Procter & Gamble Company, Cincinnati, OH (US)

( * ) Notice: Subject to any disclaimer, the term of this patent is extended or adjusted under 35 U.S.C. 154(b) by 476 days.

(21) Appl. No.: 10/428,246

(22) Filed: May 2, 2003
(Under 37 CFR 1.47)

(65) Prior Publication Data
US 2004/0097398 A1    May 20, 2004

Related U.S. Application Data

(63) Continuation of application No. PCT/US01/45017, filed on Oct. 31, 2001.

(30) Foreign Application Priority Data

Nov. 3, 2000    (EP)    .................................. 00650180

(51) Int. Cl.
*A61Q 13/00*    (2006.01)
(52) U.S. Cl. .............................................. 512/2; 512/4
(58) Field of Classification Search .................... 512/2, 512/4
See application file for complete search history.

(56) References Cited

U.S. PATENT DOCUMENTS

| | | | |
|---|---|---|---|
| 3,939,099 A | | 2/1976 | Tusa et al. |
| 4,678,598 A | | 7/1987 | Ogino et al. |
| 5,238,915 A | | 8/1993 | Fuwa et al. |
| 6,033,679 A | | 3/2000 | Woo et al. |
| 2003/0087776 A1* | | 5/2003 | Heltovics et al. ........... 510/101 |
| 2003/0119713 A1* | | 6/2003 | Heltovics et al. .............. 512/4 |
| 2003/0211125 A1* | | 11/2003 | Heltovics et al. ........... 424/401 |
| 2004/0091628 A1* | | 5/2004 | Heltovics et al. ........... 427/402 |

FOREIGN PATENT DOCUMENTS

| EP | 0 303 461 B1 | 12/1992 |
|---|---|---|
| JP | 58052211 | 3/1983 |
| JP | 63-192706 | 8/1988 |
| JP | 06287127 | 10/1994 |
| JP | 176587 A | 7/1996 |
| JP | 183719 A | 7/1996 |
| JP | 120541 A | 5/1998 |
| WO | WO 98/07405 | 2/1998 |
| WO | WO 98/47477 | 10/1998 |
| WO | WO 98/47478 | 10/1998 |
| WO | WO 99/43667 | 9/1999 |
| WO | WO 02/089833 A2 | 11/2002 |

* cited by examiner

*Primary Examiner*—Monique T. Cole
(74) *Attorney, Agent, or Firm*—Kenya T. Pierre; Andrew J. Hagerty; Tara M. Rosnell

(57) ABSTRACT

The invention provides a method for improving release, on a surface, of a fragrance from an entrapment structure of at least one fragrance oil and at least one entrapment material. The method destabilizes the entrapment structure by providing at least one trigger molecule which preferentially associates with the entrapment material; and/or at least one release agent which at least partially disrupts the entrapment structure.

The invention also provides a composition for improving release of a fragrance from a surface. The composition comprises at least one fragrance oil; at least one entrapment material, the at least one fragrance oil and the at least one entrapment material being capable, in use, of forming an entrapment structure on the surface. The composition also comprises at least one destabilizing material, which permits formation of the entrapment structure on the surface but which destabilizing material can, in use, destabilize the entrapment structure by providing at least one trigger molecule which preferentially associates with the entrapment material; and/or at least one release agent which partially disrupts the entrapment structure; and at least one compatible solvent which doesn't interfere with the formation of the entrapment structure on the surface.

The present methods and compositions can improve fragrance perception, by overcoming the differences in fragrance perception that result from different surface, for example, skin, hydration levels and/or different surface types.

38 Claims, No Drawings

METHODS AND COMPOSITIONS FOR IMPROVED FRAGRANCING OF A SURFACE

CROSS REFERENCE TO RELATED APPLICATION

This is a continuation application of International Application PCT/US01/45017, with an international filing date of Oct. 31, 2001.

FIELD OF THE INVENTION

The present invention relates to methods and compositions for improving release of a fragrance from an entrapment structure on a surface, preferably a surface of a human or animal body, such as skin or hair. The methods comprise destabilising the entrapment structure by providing a destabilising material comprising at least one trigger molecule which preferentially associates with one or more of the at least one entrapment material; and/or at least one release agent which at least partially disrupts (dissolves and/or lyses) the entrapment structure. The compositions comprise at least one fragrance oil, at least one entrapment material, the at least one fragrance oil and the at least one entrapment material being capable, in use, of forming an entrapment structure on the surface; at least one destabilising material which permits formation of the entrapment structure on the surface and which destabilises, in use, the entrapment structure on the surface; and at least one compatible solvent which does not interfere with formation of the entrapment structure on the surface. More particularly, this invention relates to methods and compositions wherein, over time, the entrapment structure is destabilised, thus allowing a more efficient release of fragrance. Methods and compositions of the present invention are suitable for application to a wide variety of surfaces but particularly to the skin and hair.

BACKGROUND TO THE INVENTION

It has long been a feature of many types of compositions, including cosmetic compositions, that they comprise a fragrance oil for the purpose of delivering a pleasant smell. This can improve the overall consumer acceptance of the composition or mask unpleasant odours. In fact, it can be the sole purpose of some compositions to impart a pleasant odour to the skin, hair or other suitable surface.

The fragrance oil(s) used within fragrance compositions usually comprise many different perfume raw materials. Each of these perfume raw materials differs from another by several important properties including individual character, volatility, olfactory detection (known as the odour detection threshold) and the like. By bearing in mind these different properties, and others, fragrance oils, with an overall specific character profile, are developed by blending various perfume raw materials. It is usual that the character is designed to develop, alter and mature over time as the different perfume raw materials evaporate from the surface and are detected by the user. For example, perfume raw materials which have a high volatility are commonly used within a fragrance oil to give light, fresh, fruity, citrus, green or delicate floral characters to the fragrance oil which are detected soon after application. Such materials are usually referred to in the field of fragrances as "top notes". By way of a contrast, the less volatile perfume raw materials are typically used to give characters such as musk, sweet, balsamic, spicy, woody or heavy floral to the fragrance oil which, although may be detected soon after application, also last for longer. These materials are usually referred to as "middle notes" or "base notes". Highly skilled perfumers are generally employed to carefully blend perfume raw materials so that the resultant fragrance oils have the desired overall fragrance character profile.

To date, the physical characteristics of the perfume raw materials has been one of the limiting factors for perfumers when designing specific fragrance characters. This is because the volatisation rate of any given ingredient has been mainly related to its boiling point and is therefore out of the control of the perfumer. The result has been that it has only been possible to develop fragrance oils which impart a "top note" character for a short period of time. This is because the top note perfume raw materials are highly volatile and therefore rapidly evaporate from the surface. Therefore, any lasting element of a fragrance has been achieved by using middle and base notes, which in turn restricts the achievable characters. Blending of higher levels of top note perfume raw materials to a fragrance oil does not improve the long lasting nature of the light, fresh, fruity, citrus, green, or delicate floral "top note" fragrance character, but instead may result in a stronger initial burst which still quickly evaporates.

In addition, the physical properties of the surface to which the fragrance composition is applied can also affect the perceived fragrance character. This is because the interaction between the individual perfume raw materials and the surface can also affect the volatisation rate of the fragrance. This is particularly true for human skin, a highly variable surface. For example, consumers with oily skin (e.g., in summer or those living closer to the equator or younger people) often perceive a change in fragrance strength and duration as a result of the fragrance oil becoming dissolved in their skin sebum. Similarly, skin hydration levels can vary between individuals with different skin types (e.g. dry versus normal skin) and/or can vary through the influence of external factors such as weather (skin hydration levels are usually lower in winter), geographical factors (those living at northerly latitudes have lower skin hydration levels than those living nearer the equator) and age. Such varying skin hydration levels can result in dissolution of varying amounts of different fragrance oils, to different extents. Thus, skin hydration levels also impact fragrance performance on the skin. Since skin hydration and sebum levels can vary considerably, this can have a large impact on the consumer perception of a particular fragrance.

It is known that consumer preference for fragrance compositions is mostly driven by the initial character perceived soon after application which often comprises a high level of "top notes". It is therefore desirable for the user to be able to perceive long lasting initial fragrance character, including long lasting "top note" character. As such, it would be advantageous to be able to tailor a composition, which performs advantageously on different skin types (see above) and which will develop, in a new way, unique fragrance characteristics wherein the release rate of one, or several, well recognised fragrance characters, particularly "top note" fragrance characters, is controlled by factors other than the physical characteristics of the perfume raw materials and the surface (for example, skin type), in order that the fragrance character can be maintained over a substantial period of time. In this way it will be possible to tailor fragrances with unique long lasting, "top, middle and base note" character which consumers with varying surface, especially skin, types will be able to experience. Equally, it is possible to create fragrances with unique long lasting, "top, middle and base note" character, which overcome the variability of fragrance experiences that can result from different surface types.

In the past, many attempts have been made to alter and prolong the volatility profiles of fragrance oils to extend the overall fragrance effect within many types of compositions. For instance, the fragrance oil may be formulated to include a higher proportion of perfume raw materials with a low volatility, i.e. of middle and base note character. However, as discussed above, this restricts the fragrance character that can be achieved over time. Another approach has been to chemically, and reversibly, modify the perfume raw materials to form a pro-perfume compound such as those disclosed in patent applications WO 98/47477; WO 99/43667; WO 98/07405; WO 98/47478; all of which are incorporated herein by reference. The resultant pro-perfumes are not themselves volatile but, after the chemical modification is reversed, the perfume raw material is released and can then evaporate in the usual way. In these applications, the release rate of the perfume raw materials is controlled by the reaction rate for transforming the pro-perfume to perfume raw material. Whilst pro-perfumes can enable the delayed release of specific perfume raw materials, only a restricted range of materials are available and supply can be both limited and expensive due to difficult synthesis and proprietary commercial protection of individual compounds.

Further disclosures have discussed improving the overall longevity of a fragrance by suppressing the evaporation of the fragrance oils themselves by, for example, encapsulating the perfume raw materials (disclosed in JP-A-58/052211, EP-A-303,461); absorbing the materials to a surface, for example, by using carbon or zeolites (disclosed in U.S. Pat. No. 6,033,679); occluding the release of the perfume raw materials, for example, by the formation of a film (disclosed in U.S. Pat. No. 3,939,099); and complexing the perfume raw materials, for example, by using cyclic oligosaccharides. The prior art on this latter method includes JP-A-6/287127 and JP-A-8/176587 which disclose use of hydroxyalkylated cyclodextrins within cosmetic, single phase, alcoholic based solutions or dispersions to sustain the effect of the fragrance; and JP-A-8/183719 and JPA-10/120541 which disclose a combination of cyclodextrin encapsulated fragrance and non encapsulated fragrance within a solid, liquid or aerosol deodorant composition for prolonging the fragrance duration to at least 2 hours, all of which are incorporated herein by reference. Cyclodextrins have also been used with fragrances within cosmetic compositions to improve the solubility of the fragrance oils within the base matrix. The prior art in this area includes JP-A-62/161720 and JP-A-63/192706 which disclose the use of cyclodextrins in fragranced water based compositions. It is expected that these compositions will also have some degree of sustained fragrance release although this is not commented upon in either of these applications.

Whilst the compositions and disclosures of the prior art provide useful teachings for prolonging the fragrance character of a composition as a whole, these approaches still have limitations. Of the cyclic oligosaccharides discussed in the art, cyclodextrins are preferred, especially for fragrance compositions, since they are compatible with, and fully soluble in, a wide range of compositions. However, when used in the traditional way, cyclodextrins interact with a broad range of perfume raw materials including "top, middle and base notes" to form a stable complex which slowly, over time, releases the overall fragrance character. Moreover, these complexes can be so thermodynamically stable that only a very small amount of the complexed fragrance is released over time, sometimes at such a low, and substantially constant, level that it is not noticeable to the user. As such, when used in the traditional way, it is not uncommon for a large amount of the cyclodextrin complexed fragrance to be unused because it remains within the stable complex throughout usage and is unable to evaporate. This results in either a sub-optimal consumer experience or in the manufacturer having to use higher levels of expensive perfume raw materials and/or of entrapment materials (which could lead to poor aesthetics), in order to achieve the desired effect. As such, the prior art does not sufficiently teach how to efficiently release, over time, fragrance, particularly "top note" fragrance characters, from such complexed fragrances such that the composition has a noticeable and long lasting effect. In addition, the prior art does not teach either how to overcome the variability of fragrance experiences that can result from different surface types, in particular different skin types or how to tailor fragrances to optimise the fragrance experience for different surface types.

Surprisingly, it has now been found that release of fragrance from an entrapment structure, on the surface, of at least one fragrance oil and at least one entrapment material, can be improved by the method of destabilising the entrapment structure by providing at least one destabilising material comprising:
i) at least one trigger molecule which preferentially associates with the entrapment material; and/or
ii) at least one release agent which at least partially disrupts (dissolves and/or lyses) the entrapment structure.

Surprisingly, it has also now been found that, within compositions comprising at least one fragrance oil; at least one entrapment material, the at least one fragrance oil and the at least one entrapment material being capable, in use, of forming an entrapment structure on a surface; at least one destabilising material which permits formation of the entrapment structure on the surface and which affects, in use, the decomposition rate of the entrapment structure on the surface; and at least one compatible solvent which does not interfere with formation of the entrapment structure on the surface, a more efficient release of the fragrance oil(s) from the entrapment structure can be achieved.

The method and composition herein increase, in use, the decomposition rate of the entrapment structure on the surface and, thereby, result both in a stronger and more noticeable lasting fragrance character for the user and allow for a possible reduction in the level of fragrance oil(s) that needs to be used within such an entrapment structure without the user perceiving a reduction in fragrance strength. In addition, it has also been surprisingly found that such an at least one destabilising material, when used within any composition comprising at least one fragrance oil and at least one entrapment material, can be used to more efficiently release the fragrance oil from the entrapment structure. Furthermore, it has been found that these destabilising materials can be used to overcome the differences in fragrance perception that can result from difference in surface hydration levels and/or from different surface types.

It is known that fragrance oils and entrapment materials form chemically bonded reversible complexes either within a composition or in situ on the surface. The complex is stabilised by the formation of tertiary interactions such as Van der Waals forces and/or secondary interactions such as hydrogen bonds, between the, or each, fragrance oil and the, or each, entrapment material and the complex exists in equilibrium with uncomplexed fragrance oil(s) and entrapment material(s). On the surface, the complex(es), whether already present in the composition or, alternatively, formed, in situ, on the surface, form an amorphous or, alternatively, regular entrapment structure. In order to break down this entrapment structure, it is necessary to drive the equilibrium towards the free materials.

Whilst not wishing to be bound by theory, it is believed that the present destabilising materials can drive this equilibrium towards the free materials in one of two ways.

The first way is by using release agents which at least partially disrupt (dissolve or lyse) the entrapment structure. This can be achieved by providing dissolution agents such as dissolution solvents, for example, water or the like and/or by increasing the surface hydration levels adjacent the entrapment structure such that the available water at least partially dissolves the entrapment structure. Any materials which are able to cause an increase in the hydration level adjacent to the entrapment structure will be suitable but particularly useful are surface buffering agents, which increase the hydration level by modifying the surface proteins, and compatible and incompatible surfactants which increase the hydration level by improving the surface wetting and by enhancing the water binding. In this way, the present dissolution agents can be used to reduce variability in fragrance perception which can arise as a result of different inherent hydration levels adjacent the entrapment structure and/or to optimise fragrance perception for different surface types. The release agent can, alternatively, act by lysing the entrapment structure. Thus, when the entrapment structure is a pro-perfume, water can hydrolyse the pro-perfume, to release the fragrance. Other solvents can, similarly, lyse the pro-perfume, again to release the fragrance.

The second way that the destabilising materials can drive the entrapment structure to the free state is by providing trigger molecules which preferentially associate with the entrapment material by, for example, actively breaking the tertiary (Van der Waals) and/or secondary (hydrogen bonds) forces that hold the entrapment structure in a thermodynamically stable form. This can be achieved by the use of C1–C15 carboxylic acids, their amides, their esters and their salts which are able to form hydrogen bonds with the, or each, entrapment material, thus thermodynamically driving the breakdown of the entrapment structure. This can also be achieved by the use of incompatible surfactants which, also, preferentially associate with the entrapment material.

If the trigger molecules are to be provided within a composition which also comprises a fragrance oil and an entrapment material, it is necessary to encapsulate the trigger molecules within the composition such that the encapsulated trigger molecules permit formation of the entrapment structure on the surface but, when the trigger molecules are released over time, they then destabilise the entrapment structure by preferentially associating with the entrapment material. If the trigger molecules are to be separately provided, the invention may be enhanced by encapsulating the trigger molecules so that they are released over time, after application of the trigger molecules. Whilst not wishing to be bound by theory, it is believed that, when the trigger molecules are released over time, they delay the release of the fragrance from the entrapment structure. The invention can be still further enhanced by blending the, or each, fragrance oil such that, when it is released from the entrapment structure, it has both the desired characteristics and also the appropriate strength impact. One example is to use high odour impact "top note" perfume raw materials within the, or each, fragrance oil such that the user experiences a noticeable and long lasting "top note" character over time.

It is an object of the present invention to provide destabilising materials which are used to efficiently release the, or each, fragrance oil from the entrapment structure on the surface. It is a further object of this invention to provide destabilising materials for entrapment structures so that the entrapment structures impart long lasting unique fragrance characters that could not be achieved using traditional perfumery, for example, light, fresh, fruity, citrus, green or delicate floral "top note" fragrance character, over a prolonged time and which is independent of the surface hydration level.

It is a still further object of the present invention to provide methods for more efficiently releasing the, or each, fragrance oil from the entrapment structure. These, and other objects of this invention, will become apparent in the light of the following disclosure.

SUMMARY OF THE INVENTION

The present invention relates to a method for improving release, on a surface, of a fragrance from an entrapment structure, the entrapment structure comprising at least one fragrance oil and at least one entrapment material, the method comprising destabilising the entrapment structure by providing at least one destabilising material comprising:
  i) at least one trigger molecule which preferentially associates with one or more of the at least one entrapment material; and/or
  ii) at least one release agent which at least partially disrupts the entrapment structure.

Methods of the present invention can be tailored to improve the release of fragrance oil from the entrapment structure in which a complex is either formed in the bottle or, alternatively, is formed, in use, on the surface. Thus, for example, increased fragrance release from the entrapment structure can be provided, for use on a dry surface, such as skin with a low hydration level and/or on oily skin with a high sebum level (and vice versa). The present method improves fragrance release from fragranced compositions so as to create fragrances of varying fragrance characters, with optimised fragrance character, strength and duration profiles, for the various different surface types.

The present invention also relates to a composition for improving release, on a surface, of a fragrance, the composition comprising:
  a) at least one fragrance oil;
  b) at least one entrapment material, the at least one fragrance oil and the at least one entrapment material being capable, in use, of forming an entrapment structure on the surface;
  c) at least one destabilising material, which destabilising material permits formation of the entrapment structure on the surface and which destabilising material, in use, destabilises the entrapment structure by providing:
    i) at least one trigger molecule which preferentially associates with the entrapment material; and/or
    ii) at least one release agent which at least partially disrupts the entrapment structure; and
  d) at least one compatible solvent which doesn't interfere with formation of the entrapment structure on the surface.

Compositions of the second aspect of the present invention can be tailored to vary the release of fragrance oil from the entrapment structure formed on the surface, according to surface type. Thus, for example, if the composition is a cosmetic composition, increased fragrance release from the entrapment structure can be provided, for use on dry skin with a low hydration level and/or oily skin with a high sebum level (and vice versa). Thus, the present invention enables the creation of fragranced compositions of varying fragrance characters, with optimised fragrance character, strength and duration profiles, for the various different skin types, or, indeed, for different surface types in general.

DETAILED DESCRIPTION OF THE INVENTION

All percentages and ratios used herein are by weight of the total composition and all measurements made are at 25° C., unless otherwise designated. Unless otherwise indicated, all percentages, ratios and levels of ingredients referred to herein are based on the actual amount of the ingredient, and do not include solvent, fillers or other materials which may be combined with the ingredient in commercially available products.

All publications cited herein are hereby incorporated by reference in their entirety, unless otherwise indicated.

As used herein, the term "bloom" means a fragrance enhancement which is not intended by the user, for example, when the user unintentionally breathes on the first composition or when the user sweats.

As used herein, the term "refresh" or "refreshing" means a fragrance enhancement which is intended by the user, for example, when the user is instructed by, for example, an accompanying instruction sheet, either to breath on the first composition or to spray water or the like thereon.

The term "fragrance enhancement" as used herein is intended to embrace both fragrance blooms and fragrance refreshings as defined hereinabove.

The term "cosmetically-acceptable," as used herein, means that the compositions, or components thereof, are suitable for use in contact with a human or animal surface such as skin without undue toxicity, incompatibility, instability, allergic response, and the like.

The term "complex" as used herein, means a thermodynamically stable entity comprised of at least one fragrance oil and at least one entrapment material. Such complexes are either provided in a dissolved or dispersed form in a suitable solvent phase or, alternatively, are formed on a surface.

The term "entrapment structure" as used herein, means an amorphous (irregular) or regular crystalline, semi-solid or solid, three-dimensional association of complexes on the surface, the complexes having been provided as a solution or dispersion in a suitable composition or, alternatively, having been formed in situ on the surface.

The term "refresher composition" as used herein, means a composition containing at least one destabilising material, which refresher composition is intended to be applied to a surface, after the entrapment structure has been provided thereon.

The term "integral composition" as used herein, means a composition of the second aspect of the present invention, in which the at least one destabilising material is provided in the composition, which composition also contains at least one fragrance oil and at least one entrapment material. Thus, in such integral compositions, the entrapment structure is provided on the surface, in the presence of the at least one destabilising material.

The term "surface" as used herein, means any surface to which a fragrance might be applied and includes, but is not limited to, a surface of the human or animal body such as skin or hair, as well as surfaces such as cloth, paper, glass, and work surfaces such as laminates or the like.

The term "soluble" as used herein, means at least about 0.1 g of solute dissolves in 100 ml of solvent at 25° C. and 1 atm of pressure.

The elements of these entrapment structures from which improved release of fragrance can be achieved by the method of the present invention are described in more detail below.

Entrapment Structures

Entrapment structures comprise at least one fragrance oil and at least one entrapment material. Entrapment structures are associations of complexes on a surface, the complexes having been provided as a solution or dispersion in a suitable composition, or, alternatively, having been formed in situ on the surface.

Fragrance Oil

Compositions, preferably, comprising from about 0.01% to about 99%, preferably from about 0.25% to about 50%, more preferably from about 0.5% to about 40%, even more preferably from about 1% to about 25%, and most preferably from about 2.5% to about 25%, by weight, of the at least one fragrance oil, may be used to provide the entrapment structure on the surface.

As used herein, the term "fragrance oil" relates to a perfume raw material, or mixture of perfume raw materials, that is/are used to impart an overall pleasant odour profile to a composition. As used herein, the term "perfume raw material" relates to any chemical compound which is odiferous when in a free or un-entrapped state. In addition, "perfume raw materials" have a ClogP value preferably greater than about 0.1, more preferably greater than about 0.5, even more preferably greater than about 1.0. As used herein, the term "ClogP" means the logarithm to base 10 of the octanol/water partition coefficient. This can be readily calculated from a programme called "CLOGP" which is available from Daylight Chemical Information Systems Inc., Irvine Calif., U.S.A. Octanol/water partition coefficients are described in more detail in U.S. Pat. No. 5,578,563.

The at least one fragrance oil itself can comprise any perfume raw material suitable for use in fragrance compositions. Overall, the fragrance oil will most often be liquid at ambient temperatures and consist of a single individual perfume raw material. A wide variety of chemicals are known for fragrance uses, including materials such as aldehydes, ketones and esters. However, naturally occurring plant and animal oils and exudates comprising complex mixtures of various chemical components are also commonly known for use as fragrances. The individual perfume raw materials which comprise a known natural oil can be found by reference to journals commonly used by those skilled in the art such as "Perfume and Flavourist" or "Journal of Essential Oil Research". In addition, some perfume raw materials are supplied by the fragrance houses as mixtures in the form of proprietary speciality accords. Furthermore, the at least one fragrance oil can optionally comprise any of the fragrance oils disclosed under the heading "Fragrance Oil" in the "Compositions of the Present Invention" sub-section.

Entrapment Materials

Compositions, comprising an entrapment material preferably at a level of from about 0.001% to about 95%, preferably from about 0.01% to about 50%, more preferably from about 1% to about 25% and even more preferably from about 2% to about 8%, by weight, of the composition, may be used to provide the entrapment structure on the surface.

As defined herein, an "entrapment material" is any material which, after application to a surface and formation thereon of the entrapment structure, suppresses the volatility of the perfume raw materials within the fragrance oil, thus delaying their evaporation. It is not necessary that the entrapment material forms an association with the perfume raw material within the composition itself, only that this association exists, as the entrapment structure, on the surface after application of the composition. Non-limiting examples of mechanisms by which the delay in evaporation may occur are by the entrapment material reversibly, physically or chemically, associating with the perfume raw material through complexing, encapsulating, occluding, absorbing, binding, or otherwise adsorbing the perfume raw materials of the fragrance oil.

As defined herein, "reversible entrapment" means that any entrapment material: perfume raw material association in which the association can be broken down so that the entrapment material and perfume raw materials are released from each other. As defined herein, "chemically associated" means that the entrapment material and perfume raw material are linked through a covalent, ionic, hydrogen or other type of chemical bond. As defined herein, "physically associated" means that the entrapment material and perfume raw material are linked through a bond with a weaker force such as a Van der Waals force. For the purposes of the present invention, it is necessary that, upon the surface, the entrapment material and the perfume raw material form a reversible physical or chemical association.

As defined herein, "to delay the evaporation of a perfume raw material" means to slow down or inhibit the evaporation rate of said perfume raw material from the surface such that the fragrance character of the perfume raw material is detectable for at least 2 hours after application to the surface.

Entrapment materials for use herein are selected from polymers; capsules, microcapsules and nanocapsules; liposomes; pro-perfumes; film formers; cyclic oligosaccharides and mixtures thereof. Preferred are pro-perfumes, and cyclic oligosaccharides and mixtures thereof. Highly preferred are cyclic oligosaccharides and mixtures thereof.

Encapsulation Using Capsules, Micro-capsules and Nano-capsules

Encapsulation of fragrances within capsules, micro-capsules or nanocapsules which are broken down by environmental triggers can be used to control release of fragrance oils, by surrounding the small oil droplets as a resistant wall. This may be water sensitive so that the fragrance is released when the encapsulated particle encounters a release agent, specifically a dissolution solvent such as water, for example, moisture loss from the skin. Encapsulation techniques are well known in the art including DE 1,268,316; U.S. Pat. No. 3,539,465; and U.S. Pat. No. 3,455,838.

Moisture sensitive capsules, micro-capsules and nanocapsules are preferably formed from, but not limited to, a polysaccharide polymer. Examples of suitable polymers are dextrins, especially low-viscosity dextrins including maltodextrins. A particularly preferred example of a low viscosity dextrin is one which, as a 50% dispersion in water has a viscosity at 25° C., using a Brookfield Viscometer fitted with an "A" type T-Bar rotating at 20 rpm in helical mode, of 330±20 mPa.s. This dextrin is known as Encapsul 855 and is available from National Starch and Chemicals Ltd. A further example of a polysaccharide that can be used to form the moisture sensitive capsules is gum acacia.

Destabilising Material Sensitive Pro-Perfumes

Synthesising pro-perfumes or pro-fragrances from perfume raw materials can result in compounds which impart a delayed release mechanism to that specific perfume raw material. Pro-perfumes useful within the present invention must be sensitive to the destabilising material, specifically, the release agent. This is consistent with the objective of providing unique fragrances with a broad spectrum of "top note" characters. Compositions preferably comprising at least one pro-perfume at a level of from about 0.001% to about 50%, preferably from about 0.001% to about 25%, more preferably from about 0.01% to about 8%, by weight of the composition, may be used to provide the entrapment structure on the surface.

Within a pro-perfume, the perfume raw material has been reacted with more than one type of chemical groups such as acetal, ketal, ester, hydrolysable inorganic—organic. As such, as defined herein, the perfume raw material is considered to constitute part of the fragrance oil and the chemical groups to constitute part of the entrapment material, so that the pro-perfume as a whole constitutes the entrapment structure. Pro-perfumes themselves are designed to be non-volatile, or else have a very low volatility. However, once on the surface, the perfume raw material is released from the pro-perfume. Once released, the perfume raw material has its original characteristics. The perfume raw material may be released from the pro-perfume in a number of ways. For example, it may be released as a result of lysis using water, (hydrolysis), or by shift in an equilibrium reaction or by a pH-change. The fragrances herein can be relatively simple in their compositions, comprising a single chemical, or can comprise highly sophisticated mixtures of natural and synthetic chemical components, all chosen to provide any desired odour.

Non-limiting pro-perfumes suitable for use in the present application are described in WO 98/47477, WO 99/43667, WO 98/07405, WO 98/47478 and copending applications U.S. Ser. No. 60/105380 (23 Oct. 1998) and U.S. Ser. No. 60/130108 (20 Apr. 1999).

Cyclic Oligosaccharides

Compositions, preferably comprising from about 0.001% to about 95%, more preferably from about 0.01% to about 50%, still more preferably from about 1% to about 25%, and most preferably from about 2% to about 8%, by weight, of the at least one cyclic oligosaccharide, may be used to provide the entrapment structure on the surface.

As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and mixtures thereof and even more preferably seven saccharide units and mixtures thereof. It is common in the art to abbreviate six, seven and eight membered cyclic oligosaccharides to α, β and γ respectively.

The at least one cyclic oligosaccharide for use herein may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. The preferred cyclic oligosaccharides for use herein are α-cyclodextrins or β-cyclodextrins, or mixtures thereof, and the most preferred cyclic oligosaccharides for use herein are β-cyclodextrins.

The cyclic oligosaccharide, or mixture of cyclic oligosaccharides, for use herein may be substituted by any suitable substituent or mixture of substituents. Herein the use of the term "mixture of substituents" means that two or more different suitable substituents can be substituted onto one cyclic oligosaccharide. The derivatives of cyclodextrins consist mainly of molecules wherein some of the hydroxyl groups have been substituted. Suitable substituents include, but are not limited to, alkyl groups; hydroxyalkyl groups; dihydroxyalkyl groups; (hydroxyalkyl)alkylenyl bridging groups such as cyclodextrin glycerol ethers; aryl groups; maltosyl groups; allyl groups; benzyl groups; alkanoyl groups; cationic cyclodextrins such as those containing 2-hydroxy-3-(dimethylamino) propyl ether; quaternary ammonium groups; anionic cyclodextrins such as carboxyalkyl groups, sulphobutylether groups, sulphate groups, and succinylates; amphoteric cyclodextrins; and mixtures thereof. Other cyclodextrin derivatives are disclosed in copending application U.S. Ser. No. 09/32192 (29 May 1999), which is incorporated herein by reference.

The substituents may be saturated or unsaturated, straight or branched chain moieties. Preferred substituents include saturated and straight chain alkyl groups, hydroxyalkyl groups and mixtures thereof. Preferred alkyl and hydroxyalkyl substituents are selected from C1–C8 alkyl or hydroxyalkyl groups or mixtures thereof, more preferred alkyl and hydroxyalkyl substituents are selected from C1–C6 alkyl or hydroxyalkyl groups or mixtures thereof, even more preferred alkyl and hydroxyalkyl substituents are selected from C1–C4 alkyl or hydroxyalkyl groups and mixtures thereof. Especially preferred alkyl and hydroxyalkyl substituents are propyl, hydroxypropyl, ethyl and methyl, more especially hydroxypropyl and methyl and even more preferably methyl.

Preferred cyclic oligosaccharides for use in the present invention are unsubstituted, or are substituted by only saturated straight chain alkyl, or hydroxyalkyl, substituents. Therefore, preferred examples of cyclic oligosaccharides for use herein are α-cyclodextrin, β-cyclodextrin, methyl-α-cyclodextrin, methyl-β-cyclodextrin, hydroxypropyl-α-cyclodextrin and hydroxypropyl-β-cyclodextrin, or mixtures thereof. Most preferred examples of cyclic oligosaccharides for use herein are methyl-α-cyclodextrin and methyl-β-cyclodextrin. These are available from Wacker-Chemie GmbH, Hanns-Seidel-Platz 4, Munchen, Germany under the tradenames Alpha W6 M and Beta W7 M respectively. Especially preferred is methyl-β-cyclodextrin.

Methods of modifying cyclic oligosaccharides are well known in the art. For example, see "*Methods of Selective Modifications of Cyclodextrins*" *Chemical Reviews* (1998) Vol. 98, No. 5, pp 1977–1996, Khan et al and U.S. Pat. No. 5,710,268.

In addition to identifying the preferred substituents themselves (as outlined above), it is also preferred that the cyclic oligosaccharides have an average degree of substitution of at least 1.6, wherein the term "degree of substitution" means the average number of substituents per saccharide unit. Preferred cyclic oligosaccharides for use herein have an average degree of substitution of less than about 2.8. More preferably, the cyclic oligosaccharides for use herein have an average degree of substitution of from about 1.7 to about 2.0. The average number of substituents can be determined using common Nuclear Magnetic Resonance techniques known in the art.

The cyclic oligosaccharides are preferably soluble in both water and ethanol. As used herein, "soluble" means at least about 0.1 g of solute dissolves in 100 ml of solvent, at 25° C. and 1 atm of pressure. Preferably, the cyclic oligosaccharides for use herein have a solubility of at least about 1 g/100 ml, at 25° C. and 1 atm of pressure. Preferred is that cyclic oligosaccharides are only present at levels up to their solubility limits in a given composition at room temperature (25° C.). A person skilled in the art will recognise that the levels of cyclic oligosaccharides used in the present invention will also be dependent on the components of the entrapment structure and their levels, for example the solvents used to provide the entrapment structure on the surface or the exact fragrance oils, or combination of fragrance oils, present in the entrapment structure. Therefore, although the limits stated for the at least one oligosaccharide are preferred, they are not exhaustive.

Destabilising Materials

Any material, or mixture thereof, which is capable of destabilising the entrapment structure on the surface, is suitable for use in the method of the present invention. Such materials include at least one trigger molecule; at least one release agent; and/or mixtures of trigger molecules and release agents. Such material(s) are preferably applied in an amount of at least about 0.001%, preferably from about 0.001% to about 20%, more preferably from about 0.01% to about 15%, still more preferably from about 0.1% to about 10%, most preferably from about 0.1% to about 5%, by weight of at least one trigger molecule, or of at least one release agent or of a mixture of trigger molecules and release agents.

Trigger Molecules

Trigger molecules of the present invention act by preferentially associating with the entrapment material, over the fragrance oil.

Without wishing to be bound by theory, it is believed that the trigger molecules interact with the entrapment materials by tertiary forces such as Van der Waal's forces and/or by secondary forces such as hydrogen bonds, which interactions are thermodynamically more stable than the mainly tertiary bonds (Van der Waals' forces) that exist between the fragrance oil and the entrapment material and, thereby, the trigger molecules preferentially associate with the entrapment material. This causes, therefore, displacement of the fragrance oil from the entrapment structure. In addition, it is believed that the formation of hydrogen bonds between the entrapment material and the trigger molecule(s), also disrupts hydrogen bonds between adjacent complex molecules, thereby exposing individual complex molecules and facilitating the fragrance oil(s) to leave the individual complex molecules.

When the trigger molecule acts by breaking tertiary forces such as Van der Waals' forces and/or secondary forces such as hydrogen bonds and it is intended to formulate the trigger molecule in a composition containing an entrapment material, it is necessary that the trigger molecule is encapsulated. Such encapsulation prevents the contact (and mixing) of the encapsulated trigger molecules with the rest of the formulation prior to application and immediately after application to a surface such as the skin. After application, the encapsulated trigger molecules can be released gradually or in bursts over time by gradual (passive) or activated (active e.g. rubbing the arm) break down, decomposition or rupture of the encapsulating material. It will, of course, be appreciated by those skilled in the art that, if such trigger molecules were not separated from the rest of the formulation, they would reduce the efficacy of the entrapment material to complex with fragrance oil(s) as they would compete for the entrapment material in the initial fragrance oil—entrapment material complexation process as it occurs on the surface.

Suitable encapsulation materials include, but are not limited to capsules, microcapsules, microspheres, millicapsules, starch capsules, nanocapsules, liposomes and the like.

Suitable commercially available encapsulation materials include:

Polyoxymethylene Urea (PMU) microcapsules available from 3M Center, Building 275-5E-08, St. Paul, Minn. 55144-1000, USA; Starchosome nanocapsules available from Dragoco-Gerberdig & Co. AG, Bleichenbrücke 10, D-20354, Hamburg, Germany; Poly-Pore® adsorptive polymers (Allyl Methacrylates Crosspolymer) available from Chemdal Corp., 1500 West Shure Drive, Arlington Heights, Ill. 60004 USA; microcapsules, microspheres, millicapsules and plurilamellar multivesicular liposomes (PML) from Liptec S.A., Santa Eulália, 240 Ed. Vanguard 08902, L'hospitalet De Llobregat, Barcelona, Spain; and Primaspheres (microcapsules and microspheres) from Cognis.

It is necessary that the trigger molecules within compositions of the present invention (integral compositions) are encapsulated.

Methods of the present invention preferably comprise applying from about 0.001%, more preferably from about 0.001% to about 20%, even more preferably from about 0.01% to about 15%, still more preferably from about 0.1% to about 10%, most preferably from about 0.1% to about 5%, by weight, of at least one trigger molecule.

If the at least one trigger molecule is to be provided in an integral composition which also comprises at least one fragrance oil and at least one entrapment material, it will be necessary to encapsulate the, or each, trigger molecule in order to prevent contact of the at least one trigger molecule with the at least one entrapment material in the formulation and prior to, or during, application to a surface, since the trigger molecule is capable, of itself, of complexing with the entrapment material. This is because, since the trigger molecule is so capable, such a trigger molecule, if not encapsulated, would reduce the ability of the entrapment material to complex with the at least one fragrance oil and, thereby, form the entrapment structure, when the composition is applied onto a surface. It will, of course, be appreciated that, if the trigger molecule is to be applied to a surface after the entrapment structure is formed, i.e., in a refresher composition, then the encapsulation is not necessary but may still be desired, if delayed contact between the, or each, trigger molecule and the entrapment structure, is desired.

Any compound, or mixture of compounds, which is known to break tertiary forces such as Van der Waals forces and/or secondary forces such as hydrogen bonds within entrapment structures are useful within the present invention as trigger molecules, provided that they are chemically and physically compatible with any other essential components (of the composition, if the trigger molecules are provided in a composition), and provide the desired characteristic of destabilising the entrapment structure by preferentially associating with the entrapment material. Suitable trigger molecules include carboxylic acids, their amides, esters and salts; incompatible surfactants, and mixtures thereof.

Carboxylic Acids, Amides, Esters and Salts

Preferred trigger molecules are substituted or unsubstituted, straight or branched chain carboxylic acids, their amides, esters and salts with a chain length of C1 to C15, more preferably C1 to C8 and even more preferably C1 to C5 such as, but not limited to, formic, acetic, propionic, butyric, isobutyric, valeric, isovaleric and pivalic acids, their amides, salts and esters. Urea is a suitable agent. Such trigger molecules in an amount of from about 0.001%, preferably from about 0.001% to about 20%, more preferably about 0.01% to about 15%, even more preferably about 0.1% to about 10%, still more preferably from about 0.1% to about 5%, by weight, may be applied in the present method.

Incompatible Surfactants

Any known or conventional incompatible surfactants can be used as trigger molecules in the present method, provided that the selected agent provides the desired characteristics of destabilising the entrapment structure on the surface. Suitable surfactants include nonionic, anionic, amphoteric and zwitterionic surfactants and mixtures thereof.

From about 0.001%, preferably from about 0.001% to about 20%, more preferably from about 0.01% to about 15%, even more preferably from about 0.1% to about 10%, still more preferably from about 0.1% to about 5%, by weight, of at least one suitable incompatible surfactant, may be applied in the present method.

It is essential that the, or each, surfactant is not compatible with the entrapment material. Without wishing to be bound by theory, it is believed that such non-compatible surfactants can compete, with the at least one fragrance oil, for binding to the entrapment material—this serves to destabilise the entrapment structure.

The important parameter in identifying incompatible surfactants is its complexation constant with the entrapment material, which must be greater than about 5,000M-1, preferably greater than about 6,000M-1 and more preferably greater than about 7,000M-1. Complexation constants can be measured according to the Test Method described in U.S. Pat. No. 5,942,217.

Suitable incompatible surfactants can also be readily identified by the effect of entrapment material on the surface tension provided by the surfactant. This can be achieved by determining the surface tension (in dyne/cm) of aqueous solutions of the surface in the presence and in the absence of about 1% of a specific entrapment material in the solutions. Thus, if the surface tension, at a given concentration in water, differs by more than about 10% from the surface tension of the same surfactant in the 1% solution of the entrapment material, this indicates a strong interaction between the surfactant and the entrapment material and, therefore, an incompatible surfactant.

Useful incompatible surfactants include sodium dodecyl sulfate and dodecanolpoly(6)ethoxylate, which as entrapment material-incompatible surfactants, are strongly interactive, with more than a 10% elevation in surface tension in the presence of a typical cyclodextrin like hydroxypropyl beta-cyclic oligosaccharide and methylated beta-cyclic oligosaccharide.

Among the nonionic surfactants that are useful herein are those that can be broadly defined as condensation products of long chain alcohols, e.g. C8–30 alcohols, with sugar or starch polymers i.e. glycosides. Other useful nonionic surfactants include the condensation products of alkylene oxides with fatty acids (i.e. alkylene oxide esters of fatty acids). These materials have the general formula RCO(X)nOH wherein R is a C10–30 alkyl group, X is —OCH2CH2— (i.e. derived from ethylene glycol or oxide) or —OCH2CHCH3— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula RCO(X)nOOCR wherein R is a C10–30 alkyl group, X is —OCH2CH2— (i.e. derived from ethylene glycol or oxide) or —OCH2CHCH3—(i.e. derived from propylene glycol or oxide), and n is an integer from about 6 to about 100. Even further suitable examples include a mixture of cetearyl alcohols, cetearyl glucosides such as those available under the trade name Montanov 68 from Seppic.

The surfactants useful herein can alternatively or additionally include any of a wide variety of cationic, anionic, zwitterionic, and amphoteric surfactants such as are known in the art. See, e.g., McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973. A wide variety of anionic surfactants are also useful herein. See, e.g., U.S. Pat. No. 3,929,678, to Laughlin et al., issued Dec. 30, 1975.

A wide variety of anionic surfactants are also useful herein. See, e.g., U.S. Pat. No. 3,929,678, to Laughlin et al., issued Dec. 30, 1975. Exemplary anionic surfactants include the alkoyl isethionates (e.g., C12–C30), alkyl and alkyl ether sulfates and salts thereof, alkyl and alkyl ether phosphates and salts thereof, alkyl methyl taurates (e.g., C12–C30), and soaps (e.g., alkali metal salts, e.g., sodium or potassium salts) of fatty acids.

Amphoteric and zwitterionic surfactants are also useful herein. Examples of amphoteric and zwitterionic surfactants which can be used herein are those which are broadly described as derivatives of aliphatic secondary and tertiary amines in which the aliphatic radical can be straight or branched chain and wherein one of the aliphatic substituents contains from about 8 to about 22 carbon atoms (preferably C8–C18) and one contains an anionic water solubilising group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, and branched and unbranched alkanoyl sarcosinates, and mixtures thereof.

Release Agents

Any agent, or mixture thereof, which is capable of at least partially disrupting the entrapment structure on the surface, is suitable for use in the present method.

Such agents include, but are limited to, agents which at least partially disrupt the entrapment structure by either dissolving and/or lysing the entrapment structure using dissolution agents; lysis agents, or a mixture thereof.

Such release agents may be encapsulated in, for example, a capsule, microcapsule, microsphere, millicapsule, starch capsule, nanocapsule or the like, if it is desired to delay interaction of the release agent(s) with the entrapment structure.

Dissolution Agents

Any agent, or mixture thereof, which is capable of at least partially dissolving the entrapment structure on the surface, is suitable for use in the method of the present invention. Such agents include, but are not limited to, agents which directly dissolve (at least partially) the entrapment structure, i.e., dissolution solvents including water and other solvents and agents which indirectly lead to at least partial dissolution of the entrapment structure, including pH buffering materials and both compatible and incompatible surfactants, whose use leads to increased hydration of the entrapment structure. Mixtures of direct-acting agents; mixtures of indirect-acting agents; and mixtures of direct-acting and indirect-acting agents are also contemplated by the present invention.

Water

The methods of the present invention may comprise water or any other suitable dissolution solvent as a dissolution agent.

Alternatively, the hydration level of surfaces such as human skin can be indirectly affected in two main ways, by use of pH buffering materials or by use of entrapment material compatible and incompatible surfactants. The hydration level of other surfaces can be indirectly affected by the use of entrapment material-compatible and incompatible surfactants.

pH Buffering Materials pH buffering materials useful herein include any agents which can be safely applied to the surface such as the skin. It will, of course, be appreciated that pH buffering materials which can directly interact with the at least one entrapment material, reduce the ability of said entrapment material to complex with the at least one fragrance oil and, for the integral composition, it is necessary to encapsulate such pH buffering materials. The purpose of encapsulation is to prevent the contact (and mixing) of the encapsulated pH buffering materials with the rest of the formulation of the integral composition prior to and immediately after application to the surface such as skin, if the pH buffering materials can interact with the entrapment material. As will be appreciated by those skilled in the art, if the pH buffering materials which can strongly interact with at least one entrapment material were not separated from the rest of the formula, they would reduce the efficacy of the entrapment material to complex with the fragrance oil(s) as they would compete for the entrapment material in the initial entrapment structure formation process as the process occurs on the surface.

In order to be effective, it is necessary that the buffering agent acts to locally change the pH of a surface such as the skin to at least one pH unit above, or below, the usual pH range (usual range for skin is 5.0–5.5). As such, it is preferred that that pH buffering material is applied at such a level that the pH of the composition is less than 4.0, or greater than 6.5; more preferably such that the pH of the composition is between 3.0 and 4.0 or between 9.0 and 10.0 and most preferably such that the pH of the composition is about 3.0 or about 10.0.

Acidic pH buffering materials i.e. materials to reduce surface pH, in particular the skin pH to below its usual pH range of 5.0–5.5 include, but are not limited to salicylic acid (o hydroxy benzoic acid) (which can interact with certain cyclic oligosaccharides, so as to destabilise the entrapment structure) or other suitable beta-hydroxy acid(s) such as citric acid; alpha-hydroxy acids, such as glycolic acid; as well as salts thereof and/or mixtures thereof.

Suitable basic pH buffering materials i.e. materials to increase surface pH, in particular the skin pH to above its usual pH range of 5.0–5.5 include, but are not limited to sodium carbonate and/or sodium bicarbonate; trisodium citrate; phosphate/hydrogen phosphate buffer systems as well as salts thereof, where appropriate, and/or mixtures thereof.

Other pH buffer systems to achieve varying levels of pH include, but are not limited to, tetroxalate, tartrate, phthalate and borax buffer systems, or mixtures thereof. A range of suitable pH buffering materials can be found in a number of references including Handbook of Chemistry and Physics 55th Edition, 1974–1975 CRC Press, INC and Vogel's Text Book of Quantitative Chemical Analysis, 5th Edition, Longman Scientific and Technical, 1989, both of which are incorporated herein by reference.

Entrapment Material-Compatible Surfactants

Any known or conventional entrapment material-compatible surfactants can be used in the method of the present invention, provided that the selected agent is also chemically and physically compatible with the any other essential components, and provides the desired characteristics. Suitable surfactants include nonionic, anionic, amphoteric and zwitterionic surfactants and mixtures thereof.

Preferably from about 0.001%, more preferably from about 0.001% to about 20%, still more preferably about 0.01% to about 15%, even more preferably about 0.1% to about 10%, still more preferably about 0.1% to about 5%, by weight, of at least one suitable surfactant, may be applied in the present method.

As used herein, the term "entrapment material-compatible surfactant" relates to any surfactant which does not interact with entrapment material either in the product matrix, nor once applied on the surface. This is important because it means that such surfactants do not bind with the entrapment material. Therefore, such surfactants can be used, uncapsulated, in the product matrix because such surfactants will not compete for binding with the entrapment material either on the surface, or in the bottle. This means that the efficacy of entrapment material to complex fragrance oil on the skin is maintained, and the effect of entrapment material can be targeted to increase the surface hydration level only.

The compatible surfactant should not substantially form a complex with the entrapment material so as to diminish performance of the entrapment material and/or the surfactant. Complex formation diminishes both the ability of the entrapment material to complex with the at least one fragrance oil and the ability of the surfactant to lower the surface tension of the surface.

The important parameter in identifying entrapment material-compatible surfactants is its complexation constant with entrapment material, which is no greater than about 5,000 M-1, preferably no greater than about 4,000 M-1, and more preferably no greater than about 3,000 M-1. Complexation constants can be measured according to the Test Method described in U.S. Pat. No. 5,942,217.

Suitable entrapment material-compatible surfactants can also be readily identified by the absence of effect of entrapment material on the surface tension provided by the surfactant. This is achieved by determining the surface tension (in dyne/cm) of aqueous solutions of the surfactant in the presence and in the absence of about 1% of a specific entrapment material in the solutions. The aqueous solutions contain surfactant at concentrations of approximately 0.5%, 0.1%, 0.01%, and 0.005%. The entrapment material can affect the surface activity of a surfactant by elevating the surface tension of the surfactant solution. If the surface tension at a given concentration in water differs by more than about 10% from the surface tension of the same surfactant in the 1% solution of the entrapment material, that is an indication of a strong interaction between the surfactant and the entrapment material. The preferred surfactants herein should have a surface tension in an aqueous solution that is different (lower) by less than about 10%, preferably less than about 5%, and more preferably less than about 1% from that of the same concentration solution containing 1% entrapment material.

The entrapment material-compatible surfactants herein are preferably either weakly interactive with entrapment material (less than 5% elevation in surface tension), or non-interactive (less than 1% elevation in surface tension).

Useful entrapment material-compatible surfactants in the present compositions include, but are not limited to, entrapment material-compatible surfactants selected from the group consisting of: block copolymer surfactant, siloxane surfactant, anionic surfactant, castor oil surfactant, sorbitan ester surfactant, polyethoxylated fatty alcohol surfactant, polypropoxylated fatty alcohol surfactant, glycerol mono-fatty acid ester surfactant, polyethylene glycol fatty acid ester surfactant, polypropylene glycol fatty acid ester surfactant, fluorocarbon surfactant, and mixtures thereof. The entrapment material-compatible surfactants used in the present methods are preferably selected from the group consisting of castor oil surfactant, sorbitan ester surfactant, polyethoxylated fatty alcohol surfactant, polypropoxylated fatty alcohol surfactant, glycerol mono-fatty acid ester surfactant, polyethylene glycol fatty acid ester surfactant, polypropylene glycol fatty acid ester surfactant, fluorocarbon surfactant, and mixtures thereof. In this connection, suitable surfactants are disclosed in, for example, U.S. Pat. No. 5,955,093, U.S. Pat. No. 5,968,404 and U.S. Pat. No. 6,033,679, all of which are incorporated herein by reference.

Preferred surfactants are silicon co-polyol surfactants: Silwet type of surfactant, particularly with EO/PO mixtures (e.g. Silwet L-7001 and L-7002). Also preferred are Laureth-23, dimethicone copoyol and/or cetyl betane. Such preferred surfactants are associated with superior feel (smooth, silky and non-sticky) and have improved ease of spread.

Entrapment Material-Incompatible Surfactants

Any known incompatible surfactants, such as those described under the section "Trigger Molecules", also act as indirect dissolution agents by increasing surface hydration.

Lysis Agents

Any agent, or mixture thereof, which is capable of at least partially lysing the entrapment structure, to release the at least one fragrance oil, is suitable for use in the present method. Such lysis agents include water which can, in use, hydrolyse an entrapment structure comprising, for example, a pro-perfume, so as to release the fragrance. Any other suitable lysis agents are also contemplated for use in the present method.

Compositions of the Present Invention

Fragrance Oil

Integral compositions according to the present invention optionally comprise from about 0.01% to about 99%, by weight, of at least one aesthetically acceptable fragrance oil. Preferably, the integral compositions comprise from about 0.25% to about 50%, more preferably from about 0.5% to about 40%, still more preferably from about 1% to about 25% and most preferably from about 2.5% to about 25%, by weight, of the at least one fragrance oil. The, or each, fragrance oil in the integral composition can be the same or different, from the, or each, fragrance oil of the entrapment structure as described above.

In order that fragrance oils can be developed with the appropriate character for the present invention, the perfume raw materials have been classified based upon two key physical characteristics:
(i) boiling point (BP) measured at 1 atmosphere pressure. The boiling point of many fragrance materials are given in Perfume and Flavour Chemicals (Aroma Chemicals), Steffen Arctander (1969). Perfume raw materials for use in the present invention are divided into volatile perfume raw materials (which have a boiling point of less than, or equal to, about 250° C.) and residual perfume raw materials (which have a boiling point of greater than about 250° C., preferably greater than about 275° C.). Volatile perfume raw materials, for the purposes of this invention, are considered to be those that impart "top note" i.e., light, fresh, fruity, citrus, green or delicate floral characters to the at least one fragrance oil and the like. Similarly, the residual perfume raw materials are considered to be those that impart "middle or base note" i.e., musk, sweet, balsamic, spicy, woody or heavy floral characters to the at least one fragrance oil and the like. All perfume raw materials will preferably have boiling points (BP) of about 500° C. or lower.

(ii) odour detection threshold which is defined as the lowest vapour concentration of that material which can be olfactorily detected. The odour detection threshold and some odour detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalar, editor ASTM Data Series DS 48A, American Society for Testing and Materials, 1978, both of said publications being incorporated by reference. Perfume raw materials for use in the present invention can be classified as those with a low odour detection threshold of less than, or equal to, 50 parts per billion, preferably less than, or equal to, 10 parts per billion and those with a high odour detection threshold which are detectable at greater than 50 parts per billion (values as determined from the references above).

Since, in general, perfume raw materials refer to a single individual compound, their physical properties (such as ClogP, boiling point, odour detection threshold) can be found by referencing the texts cited above. In the case that the perfume raw material is a natural oil, which comprises a mixture of several compounds, the physical properties of the complete oil should be taken as the weighted average of the individual components. In the case that the perfume raw material is a proprietary speciality accord, its physical properties should be obtained from the supplier.

Fragrance oils for use in the present invention can comprise any mixture of known perfume raw materials such that the desired overall character is achieved. In general, a broad range of suitable perfume raw materials can be found in U.S. Pat. No. 4,145,184, U.S. Pat. No. 4,209,417, U.S. Pat. No. 4,515,705, and U.S. Pat. No. 4,152,272. Non-limiting examples of perfume raw materials which are useful for blending to formulate fragrance oil(s) for use in the present invention are given below. Any perfume raw materials, natural oils or proprietary speciality accords known to a person skilled in the art can be used within the present invention.

However, it is preferred that the at least one fragrance oil for use in the entrapment structure comprises about 5% or greater, preferably from about 5% to about 99%, more preferably from about 5% to about 70%, still more preferably from about 10% to about 60%, and even more preferably from about 25% to about 60%, by weight of the at least one fragrance oil, of volatile "top note" perfume raw material(s), i.e., materials having a boiling point of less than, or equal to, about 250° C. It is also preferred that the at least one fragrance oil also comprises from about 0.01% to about 95%, preferably from about 5% to about 85%, more preferably from about 10% to about 60%, by weight of the at least one fragrance oil, of the residual "middle and base note" perfume raw materials, i.e., materials having a boiling point of greater than about 250° C. Furthermore, it is preferred that the weight ratio of volatile "top note" to residual "middle and base notes" perfume raw materials within the at least one fragrance oil is in the range from about 1:20 to about 20:1, preferably from about 1:10 to about 10:1, more preferably from about 8:1 to about 1:2, most preferably from about 1.2:1 to about 1:1.2.

Furthermore, it is preferred that, within the at least one fragrance oil, perfume raw materials are used which have a low odour detection threshold. It is preferred for use herein that the "top note" perfume raw materials within the at least one fragrance oil comprise 5% or greater, by weight of the "top note" perfume raw materials, of "top note" perfume raw materials which have an odour detection level of less than, or equal to, 50 parts per billion, preferably less than, or equal to, 10 parts per billion. In addition, it is highly preferred that the "middle or base note" perfume raw materials within the fragrance oil comprise 10% or greater, more preferably 20% or greater and most preferably 50% or greater, by weight of the "middle or base note" raw materials, of "middle notes" or "base notes", or a mixture thereof, with an odour detection threshold of less than, or equal to, 50 parts per billion, preferably less than, or equal to, 10 parts per billion. Since materials with low odour detection levels can be detected when only very small levels are present, they are particularly useful for developing the long lasting character of the at least one fragrance oil released over time from the entrapment structure on the surface.

Volatile perfume raw materials ("top notes") useful in the present invention are selected from, but are not limited to, aldehydes with a relative molecular mass of less than or equal to about 200, esters with a relative molecular mass of less than or equal to about 225, terpenes with a relative molecular mass of less than or equal to about 200, alcohols with a relative molecular mass of less than or equal to about 200, ketones with a relative molecular mass of less than or equal to about 200, nitriles, pyrazines, and mixtures thereof.

Examples of volatile "top note" perfume raw materials having a boiling point of less than, or equal to, 250° C., with a low odour detection are selected from, but are not limited to, anethol, methyl heptine carbonate, ethyl acetoacetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde and octyl aldehyde. Further examples of volatile perfume raw materials having a boiling point of less than, or equal to, 250° C., which are generally known to have a low odour detection threshold include, but are not limited to, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, isopropyl quinoline, 2,6-nonadien-1-ol, 2-methoxy-3-(2methylpropyl)-pyrazine, methyl octine carbonate, tridecene-2-nitrile, allyl amyl glycolate, cyclogalbanate, cyclal C, melonal, gamma nonalactone and cis 1,3-oxathiane-2-methyl4-propyl.

Other volatile "top note" perfume raw materials having a boiling point of less than, or equal to, 250° C., which are useful in the present invention, and which have a high odour detection threshold, are selected from, but are not limited to, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox and cis-3-hexenyl acetate.

Examples of residual "middle and base note" perfume raw materials having a boiling point of greater than 250° C., and which have a low odour detection threshold, are selected from, but are not limited to, ethyl methyl phenyl glycidate, ethyl vanillin, heliotropin, indol, methyl anthranilate, vanillin, amyl salicylate and coumarin. Further examples of residual perfume raw materials having a boiling point of greater than 250° C., and which are generally known to have a low odour detection threshold, include, but are not limited to, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxyl phenyl butanone, 8-cyclohexadecen-1-one, oxocyclohexadecen-2-one/habanolide, florhydral and intreleven aldehyde.

Other residual "middle and base note" perfume raw materials having a boiling point of greater than 250° C. which are useful in the present invention, and which have a high odour detection threshold, are selected from, but are not limited to, eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide and phenoxy ethyl propionate.

Entrapment Material

Integral compositions of the present invention optionally comprise from about 0.001% to about 40%, preferably from about 0.1% to about 30%, more preferably from about 2.5% to about 25%, even more preferably from about 5% to about 20%, still more preferably from about 10% to about 15% and most preferably from about 2% to about 8%, by weight, of at least one entrapment material. The, or each, entrapment material can be the same or different from the, or each, entrapment material of the entrapment structure as described above.

Destabilising Material

Integral compositions of the present invention comprise at least one destabilising material selected from trigger molecule(s), release agent(s) and mixtures thereof. The, or each, destabilising material can be the same or different from the, or each, destabilising material as described above in relation to the method of the present invention with the exception that the, or each, trigger molecule must be encapsulated, as is described above.

Compatible Solvent

Integral compositions of the present invention comprise at least one compatible solvent which doesn't interfere with formation of the entrapment structure on the surface. A suitable solvent may be volatile or non-volatile or can comprise a mixture of suitable volatile and nonvolatile solvents. Compositions of the present invention preferably comprise greater than about 50%, more preferably from about 55% to about 99.9%, even more preferably from about 60% to about 95%, by weight, of a suitable solvent or a mixture thereof.

Integral compositions of the present invention preferably comprise greater than about 50%, more preferably from about 55% to about 99.9%, still more preferably from about 60% to about 95%, by weight, of a volatile compatible solvent, or mixture of volatile solvents. Any volatile solvent suitable for use in the compositions can be used herein. The solvents for use herein are preferably organic, odourless, volatile solvents.

As used herein, "volatile" refers to substances having a boiling point under 1 atm, of less than about 95° C., more preferably less than about 90° C., even more preferably less than about 85° C., and even more preferably still less than about 80° C. As used herein, "non-volatile" refers to substances having a boiling point under 1 atm of greater than, or equal to, 95° C.

Preferably the volatile solvent(s) for use herein will be safe for use on a wide range of surfaces, more preferably on human or animal skin or hair. Suitable volatile solvents include, but are not limited to, those found in the *CTFA International Cosmetic Ingredient Dictionary and Handbook,* 7th edition, volume 2 P1670–1672, edited by Wenninger and McEwen (*The Cosmetic, Toiletry, and Fragrance Association, Inc., Washington, D.C.,* 1997). Conventionally used volatile solvents include C3–C14 saturated and unsaturated, straight or branched chain hydrocarbons such as cyclohexane, hexane, isopentane, pentane, halogenated alkanes such as perfluorodecalin; ethers such as dimethyl ether, diethyl ether; straight or branched chain alcohols and diols such as methanol, ethanol, isopropanol, t-butyl alcohol, butoxypropanol, isopentyldiol; aldehydes and ketones such as acetone; propellants, and mixtures thereof. Preferred volatile solvents are ethers such as diethyl ether; straight or branched chain alcohols and diols such as methanol, ethanol, isopropanol, t-butyl alcohol, butoxypropanol, isopentyldiol; propellants, and mixtures thereof. More preferred for use herein are C1–C4 straight chain or branched chain alcohols for example methanol, ethanol, isopropanol and t-butanol and mixtures thereof, and most preferred for use herein is ethanol.

While the integral compositions of the present invention may comprise a volatile compatible solvent, they may also comprise "non-volatile" solvents, including water. Integral compositions of the present invention preferably comprise less than about 50%, more preferably from about 0.1% to about 45%, still more preferably from about 5% to about 40%, even more preferably from about 25% to about 35%, by weight, of a non-volatile solvent or a mixture of non-volatile solvents. Suitable non-volatile solvents include, but are not limited to, water, butylene glycol, volatile silicones such as cyclomethicones for example octamethyl cyclo tetrasiloxane and decamethyl cyclopentane siloxane; volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane; benzyl benzoate, diethyl phthalate, isopropyl myristate, and mixtures thereof.

Molecular Wedges

Integral compositions of the present invention may optionally include a molecular wedge. While not wishing to be limited by theory, the above mentioned molecular wedge molecules can provide, on the surface, tertiary inclusion complexes with the entrapment material of the at least one fragrance oil and the at least one cyclic oligosaccharide. These small dipolar molecules can fit into the cavity of the cyclic oligosaccharide and anchor via their hydroxyl groups onto the outside rim of the cyclic oligosaccharide through hydrogen bonding. This enables the inclusion of all or parts of the fragrance oil into the cavity of the cyclic oligosaccharide such that the stability of the formed tertiary complex is increased versus the binary complex formed by the fragrance oil and cyclic oligosaccharide alone.

Low molecular weight polyol molecular wedges having from about 2 to about 12 carbon atoms, preferably from about 2 to about 6 carbon atoms, and at least one hydroxyl functional group, preferably at least 2 hydroxyl functional groups are preferably used herein for further prolonging the fragrance character of the integral composition of the present invention. These polyols can further contain ether groups within the carbon chain. Suitable examples include ethylene glycol, propylene glycol, dipropylene glycol, 1,4-butanediol, 1,6-hexanediol and mixtures thereof. When present, these polyols are present at a level of from about 0.01% to about 20%, preferably from about 0.1% to about 10%, and especially from about 0.5% to about 5% by weight of the integral composition. It is preferred that the molar ratio of molecular wedge material to cyclic oligosaccharide is from 10:1 to 1:10, preferably 1:1 or greater, especially about 1:1.

Refresher Compositions

Fragrance Oil

Refresher compositions for use in the method of the present invention optionally comprise from about 0.001% to about 20%, by weight, of at least one aesthetically acceptable fragrance oil. The, or each, fragrance oil in the refresher composition can be the same or different, from the, or each, fragrance oil of either the entrapment structure as described above or the integral composition as described above.

The compositions herein may comprise water or any other suitable dissolution solvent as use as a dissolution agent or, alternatively, for use as a lysis agent, if the entrapment structure is a pro-perfume.

Water

Water is a preferred dissolution and/or lysis agent and, if present, the water will comprise preferably greater than about 1%, more preferably from about 1% to about 99%, still more preferably from about 2% to about 90%, even more preferably about 3% to about 85%, by weight, of the refresher composition.

Without wishing to be limited by theory, it is believed that water destabilises the entrapment structure by solubilising the entrapment structure. This releases individual complex molecules, thereby facilitating release of fragrance oil therefrom. It will, of course, be appreciated that any other solvent which can solubilise the entrapment structure can be used, with equal effect, as the, or one of the, dissolution agent(s). When the entrapment structure is a pro-perfume, it is believed that water acts by lysing the entrapment structure, to release the fragrance oil(s).

Solvent

Refresher compositions herein preferably comprise a destabilising material-compatible solvent. A suitable solvent may be volatile or non-volatile or can comprise a mixture of suitable solvents. Refresher compositions of the present invention preferably comprise greater than 1%, more preferably from about 1% to about 99%, even more preferably from about 2% to about 90%, still more preferably from about 3% to about 85%, even more preferably from about 4% to about 80%, by weight, of the refresher composition.

Refresher compositions of the present invention preferably comprise greater than 1%, more preferably from about 1% to about 99%, even more preferably from about 2% to about 90%, still more preferably from about 3% to about 85%, even more preferably from about 4% to about 80%, by weight, of a volatile solvent, or mixture of volatile solvents. Any volatile solvent suitable for use in the compositions can be used herein. The solvents for use herein are preferably organic volatile solvents.

As used herein, "volatile" refers to substances having a boiling point under 1 atm, of less than about 95° C., more preferably less than about 90° C., even more preferably less than about 85° C., and even more preferably still less than about 80° C. As used herein, "non-volatile" refers to substances having a boiling point under 1 atm, of greater than, or equal to, 95° C.

Preferably the volatile solvent(s) for use herein will be safe for use on a wide range of surfaces, more preferably on human or animal skin or hair. Suitable volatile solvents include, but are not limited to, those found in the *CTFA International Cosmetic Ingredient Dictionary and Handbook*, 7th edition, volume 2 P1670–1672, edited by Wenninger and McEwen (*The Cosmetic, Toiletry, and Fragrance Association, Inc., Washington, D.C.*, 1997). Conventionally used volatile solvents include C3–C14 saturated and unsaturated, straight or branched chain hydrocarbons such as cyclohexane, hexane, isopentane, pentane, halogenated alkanes such as perfluorodecalin; ethers such as dimethyl ether, diethyl ether; straight or branched chain alcohols and diols such as methanol, ethanol, isopropanol, t-butyl alcohol, butoxypropanol, isopentyldiol; aldehydes and ketones such as acetone; propellants, and mixtures thereof. Preferred volatile solvents are ethers such as diethyl ether; straight or branched chain alcohols and diols such as methanol, ethanol, isopropanol, t-butyl alcohol, butoxypropanol, isopentyldiol; propellants, and mixtures thereof. More preferred for use herein are C1–C4 straight chain or branched chain alcohols for example methanol, ethanol, isopropanol and t-butanol and mixtures thereof, and most preferred for use herein is ethanol.

While the refresher compositions herein may comprise a volatile solvent, they may also comprise one or more "non-volatile" solvents, other than water, as described hereinabove. Suitable non-volatile solvents include, but are not limited to, butylene glycol, volatile silicones such as cyclomethicones for example octamethyl cyclo tetrasiloxane and decamethyl cyclopentane siloxane; volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane; benzyl benzoate, diethyl phthalate, isopropyl myristate, and mixtures thereof.

Balance of Integral or Refresher Compositions

The compositions herein can contain a variety of other optional components suitable for rendering such ingredients more cosmetically or aesthetically acceptable or to provide them with additional usage benefits. Such conventional optional ingredients are well-known to those skilled in the art. These include any cosmetically acceptable ingredients such as those found in the *CTFA International Cosmetic Ingredient Dictionary and Handbook*, 7th edition, edited by Wenninger and McEwen, (*The Cosmetic, Toiletry, and Fragrance Association, Inc., Washington, D.C., 1997*).

Such optional additional ingredients that are suitable for inclusion into the present integral or refresher compositions include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, propyl paraben; dyes; pH adjusting agents such as lactic acid, citric acid, sodium citrate, succinic acid, phosphoric acid, sodium hydroxide, sodium carbonate; deodorants and anti-microbials such as farnesol and zinc phenolsulphonate; humectants such as glycerine; oils; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; silicones; solvents such as hexylene glycol; hair-hold polymers such as those described in WO-A-94/08557; salts in general, such as potassium acetate and sodium chloride and mixtures thereof. If present, these additional ingredients will preferably be present at a level of less than about 20%, more preferably less than about 10%, by weight, of total composition. More preferably, these additional ingredients will be present at a level of less than about 5%, by weight, of total composition.

Synthetic Silicate Clays

It is preferred that integral or refresher compositions herein comprise from about 0.001% to about 15%, preferably from about 0.01% to about 10%, more preferably from about 0.05% to about 5% and even more preferably from about 0.1% to about 4%, by weight, of at least one synthetic silicate clay. Any synthetic silicate clay material which has a trioctahedral smectite structure and a particle size less than 25 nm is useful in the present invention. Preferred materials are hydrous sodium lithium magnesium silicate modified with tetra sodium pyrophosphate, hydrous sodium lithium magnesium fluoro-silicate and hydrous sodium lithium magnesium silicate, all of which are available from Laporte Industries Ltd., Widnes, United Kingdom.

Without wishing to be bound by theory, it is believed that these clays exist as discs with a negatively charged face and positively charged rim. When the clays are placed in solution, the charge differential across their structure results in the clays stacking in a edge-face-edge orientation throughout the liquid which increases the viscosity of the solution such that it has the appearance of a gel. However, since the gel is held in place by a low level van der Waals electrostatic force, it can be readily disrupted by low shear such as shaking with the result that the liquid remains sprayable. However, once the shear force is removed, then the gel structure quickly reforms. When used, these properties of the clays can reduce the consumer negative of the composition dripping from the surface soon after it has been applied.

Product Forms The integral and refresher compositions for use in the present invention may take any form suitable for use, more preferably for cosmetic use. These include, but are not limited to, vapour sprays, aerosols, emulsions, lotions, liquids, creams, gels, sticks, ointments, pastes, mousses and cosmetics (e.g., semi-solid or liquid make-up, including foundations). Preferably, the integral and refresher compositions for use in the present invention take the form of a vapour spray. Compositions herein can be further added, as such, to other cosmetic compositions with which they are compatible. As such, they can be used within a solid composition or applied to any suitable surface.

The integral and refresher compositions for use in the present invention are preferably cosmetic compositions and, as such, will comprise a cosmetically acceptable carrier. The phrase "cosmetically acceptable carrier", as used herein, means one or more compatible solid or liquid fillers, diluents, extenders and the like, which are cosmetically acceptable as defined hereinabove. The term "compatible", as used herein, means that the components of the integral and refresher compositions for use in this invention are capable of being combined with the required and optional components of the present invention as outlined above, and with each other, in a manner such that there is no interaction which would substantially reduce the efficacy of the composition under ordinary use situations. The type of carrier utilised in the present invention depends on the type of product desired and may comprise, but is not limited to, solutions, aerosols, emulsions (including oil-in-water or water-in-oil), gels, solids and liposomes.

Preparation of Compositions

Compositions for use in the present invention should be prepared according to procedures usually used in fragrance delivery and that are well known and understood by those skilled in the art, whereby materials of similar phase partitioning can be added in any order. However, of course, trigger molecules which are not compatible with the entrapment materials must be encapsulated before such trigger molecules are incorporated into the formulation of the integral composition of the present invention. The incorporation of fragrance oil(s) can occur at any reasonable stage in the preparation of the overall integral composition (or refresher composition, if a fragrance oil is present). As such, the at least one fragrance oil can be prepared in its entirety, then incorporated with the at least one entrapment material before addition to the remainder of the composition. Alternatively, the entrapment material(s) can be added to the balance of the composition prior to addition of the complete fragrance oil(s). Finally it is possible to incorporate any single perfume raw material, or group of raw materials, individually before either adding these to the balance of the fragrance oil or to the balance of the composition.

Methods of Use

The present invention preferably relates to methods for improving release of a fragrance from an entrapment structure comprising a fragrance oil and an entrapment material on the surface, such that the fragrance release can be enhanced and, thereby, preferably remain detectable either for at least 2 hours after applying the refresher composition to the surface to which the entrapment structure had already been applied or, alternatively, for at least 2 hours after the integral composition is applied to the surface.

The method may improve fragrance release from any suitable surface. As used herein, the term "suitable surface" means any surface to which the present composition may be applied without an unduly adverse effect. Suitable surfaces include, but are not limited to skin or hair, especially skin. Other suitable surfaces include, but are not limited to, paper, glass and/or cloth substrates as well as work surfaces such as work tops of laminate or the like.

The preferred methods and compositions of the present invention may be used in a conventional manner for improving release of a fragrance from a suitable surface. An effective amount of the integral or refresher composition, typically from about 1 µl to about 1000 µl, preferably from about 10 µl to about 250 µl, more preferably from about 25 µl to about 100 µl, is applied to the surface. The integral or refresher composition may be applied by hand but is preferably applied utilising a vaporiser. Preferably, the integral or refresher composition is then left to dry.

All documents cited are, in relevant part, incorporated herein by reference; the citation of any document is not to be construed as an admission that it is prior art with respect to the present invention.

EXAMPLES

The following examples further illustrate the preferred embodiments within the scope of the present invention. These examples are given solely for the purposes of illustration and are not to be construed as limitations of the present invention as many variations of the invention are possible without departing from its spirit or scope. Unless otherwise indicated, all ingredients are expressed on a weight percentage of the active ingredient.

Fragrance Oil Examples 1–7

| Perfume Raw Material | 1 (%) | 2 (%) | 3 (%) | 4 (%) | 5 (%) | 6 (%) | 7 (%) |
|---|---|---|---|---|---|---|---|
| Damascone beta | 0.1 | — | — | 1.9 | — | — | — |
| Allyl amyl glycolate | 0.1 | — | — | — | — | 0.2 | 0.3 |
| Ionone beta | 3 | 2.5 | — | — | — | — | — |
| Damascone alpha | — | 0.1 | 0.1 | 2.6 | 0.2 | 0.2 | 0.2 |
| Methyl phenyl carbinyl acetate | — | 1.7 | — | — | — | 0.4 | — |
| Cyclogalbanate 4 | — | — | 1.8 | — | — | — | 0.5 |
| Rose oxide | — | — | 0.3 | — | — | — | 0.1 |
| Ethyl-2-methyl butyrate | — | — | 0.1 | — | — | — | 0.1 |
| Fructone | 0.5 | — | 2.2 | — | 0.1 | — | 0.8 |
| Flor acetate | 1 | — | 6.5 | — | — | — | 2.1 |
| Ionone alpha | 0.5 | — | 3 | 3 | 0.2 | — | 1.1 |
| Melonal | — | — | — | 1.5 | 0.3 | — | — |
| Undecylenic aldehyde | — | — | — | — | — | 0.4 | — |
| Lemon Oil, Cold Pressed | 35 | 5 | — | — | — | 0.5 | — |
| Bergamot Oil, Eco Essence | 30 | — | — | 14.5 | — | 1.5 | — |
| Cassis Base 345-L 1 | 1 | — | — | 30 | 3 | 1.0 | — |
| Menthol | 0.5 | — | — | — | — | — | — |
| Beta gamma hexenol | 0.5 | 1 | 0.6 | — | — | — | — |
| Phenyl ethyl alcohol | 2 | — | 8 | — | 0.4 | 2.5 | — |
| Phenoxy ethyl propionate | — | — | — | — | 0.6 | — | — |
| Linalool | 8 | 5 | — | — | — | 1.5 | — |
| Cis-3-hexenyl acetate | — | 0.2 | — | — | — | — | — |
| Linalyl acetate | — | 5 | — | — | — | 1.2 | — |
| Dihydro myrcenol | — | 2 | 22 | — | — | — | — |
| Citronellol | — | 10 | — | — | — | 1.5 | — |
| Benzyl acetate | — | 6 | — | — | — | 4 | — |
| Verdox | — | — | 7 | — | — | — | — |
| Triplal | — | — | 0.6 | — | — | 0.2 | — |
| Alpha terpineol | — | — | — | — | — | 1.2 | — |
| Dihydro iso jasmonate | 3.5 | 15 | — | 0.2 | — | 2 | 5 |
| Cetalox 1 | 0.5 | 0.2 | 0.3 | 2.2 | — | 0.1 | — |
| Bacdanol 2 | 0.1 | — | 1.5 | — | — | — | 1 |
| Undecalactone | 1 | 2 | 2 | — | — | 10.3 | 1 |
| Lyral 2 | 8 | 15 | 17 | — | 10 | 2 | 10 |
| Florhydral 5 | — | — | — | — | 5 | — | 2 |
| Cis-3-hexenyl salicylate | — | 2 | — | — | — | 1.2 | 2 |
| Indol | — | — | — | — | 0.5 | 0.5 | — |
| Ethyl vanillin | — | 0.8 | 0.7 | 1.3 | — | — | — |
| Heliotropin | — | — | — | — | 0.5 | — | 1.6 |
| Ebanol 5 | — | 2.0 | — | — | — | — | — |
| Gamma decalactone | — | — | — | 4.5 | 0.4 | — | — |
| Prunella 1 | — | — | — | 35.5 | 4 | — | — |
| Lilial 5 | — | — | — | 0.7 | — | 15 | 10 |
| Benzyl salicylate | — | — | — | — | 20 | 20 | 10 |
| Habanolide 100% 1 | — | 8 | 11 | 1.5 | 10 | 0.2 | 15 |
| Roselea 2 | — | — | — | 0.6 | — | — | 5 |
| Exaltolide | 2.5 | 8 | 14 | — | 12 | 0.4 | 8 |
| Hexyl cinnamic aldehyde | 2.2 | 5 | — | — | 5 | 2 | — |
| Zingerone 5 | — | 0.5 | — | — | 0.8 | — | — |
| Methyl cedrylone | — | 3 | — | — | 17 | — | 4 |
| Eugenol | — | — | 1.3 | — | — | — | 0.2 |
| Sandela 5 | — | — | — | — | — | 10 | 5 |
| Methyl dihydro jasmonate | — | — | — | — | 10 | 10 | 15 |
| Ionone gamma methyl | — | — | — | — | — | 10 | — |

1 Firmenich SA, 1 Route des Jeunes, CH-1211 Geneva 8 SWITZERLAND
2 International Flavors & Fragrances 521 W. 57th St, New York, NY 10019 USA
3 Quest International, Ashford, Kent, TN24 0LT, United Kingdom
4 Dragoco Gerberding & Co AG, D-37601 holzminden GERMANY
5 Givaudan-Roure, 19–23 voie des Bans BP98, 95101 Argenteuil Cedex, FRANCE Fragrance oil Examples 1–7 were made by mixing the stated levels of each raw material at room temperature (25° C.).

Compositions of the Present Invention (Integral Compositions)—Examples 8–27

| (% wt) | 8 | 9 | 10 | 11 | 12 | 13 | 14 |
|---|---|---|---|---|---|---|---|
| Surfactants | | | | | | | |
| Silwet L-7001 | 0.1 | 0.2 | 0.3 | 0.8 | — | 1.4 | 2.8 |
| Silwet L-7002 | 0.2 | 0.2 | 0.1 | — | 1.2 | 1.4 | 2.2 |
| Cyclic Oligosaccharide6 | 2.5 | 5 | 10 | 2.5 | 3.5 | 7 | 5 |
| Fragrance Oil | 10 | 12.5 | 15 | 1.5 | 5 | 8 | 10 |
| Ethanol | to 100 | to 100 | to 100 | to 100 | to 100 | to 100 | to 100 |
| Deionised Water | 13.57 | 12.77 | 11.61 | 14.81 | 14.05 | 12.79 | 12.45 |
| Laponite7 | — | — | — | — | — | — | 2 |

| (% wt) | 15 | 16 | 17 | 18 |
|---|---|---|---|---|
| Encapsulated pH Buffers in Polyoxymethylene Urea (PMU) microcapsules* | | | | |
| Salicylic Acid | to pH 3.5 | — | — | — |
| Glycolic Acid | — | to pH 4 | — | — |
| citric acid/sodium citrate | — | — | to pH 3 | — |
| Trisodium Citrate | — | — | — | to pH 8 |
| Cyclic Oligosaccharide6 | 2.5 | 5 | 10 | 2.5 |
| Fragrance Oil | 10 | 12.5 | 15 | 1.5 |
| Ethanol | to 100 | to 100 | to 100 | to 100 |
| Deionised Water | 13.57 | 12.77 | 11.61 | 14.81 |
| Laponite7 | — | 2 | — | — |

| (% wt) | 19 | 20 | 21 | 22 | 23 | 24 |
|---|---|---|---|---|---|---|
| Encapsulated Trigger Molecules in Polyoxymethylene Urea (PMU) microcapsules* | | | | | | |
| Urea | 0.2 | — | 4.8 | 1 | 2 | 0.3 |
| Propionic acid | — | 0.5 | 0.1 | 0.2 | 1 | 0.1 |
| Butyric Acid | — | — | 0.1 | 0.1 | 0.1 | 0.3 |
| Cyclic Oligosaccharide6 | 2.5 | 5 | 10 | 2.5 | 5 | 2.5 |
| Fragrance Oil | 10 | 12.5 | 15 | 1.5 | 12.5 | 1.5 |
| Ethanol | to 100 | to 100 | to 100 | to 100 | to 100 | to 100 |
| Deionised Water | 13.57 | 12.77 | 11.61 | 14.81 | 12.77 | 13.00 |
| Laponite7 | — | 2 | — | — | — | 1.5 |

| (% wt) | 25 | 26 | 27 | 28 |
|---|---|---|---|---|
| Surfactants | | | | |
| Silwet L-7001 | 0.1 | 0.2 | 0.3 | 0.8 |
| Silwet L-7002 | 0.2 | 0.2 | 0.1 | — |
| Encapsulated pH Buffers in Polyoxymethylene Urea (PMU) microcapsules* | | | | |
| Salicylic Acid | to pH 3.5 | — | — | — |
| Glycolic Acid | — | to pH 4 | — | — |
| citric acid/sodium citrate | — | — | to pH 3 | — |
| Trisodium Citrate | — | — | — | to pH 8 |
| Encapsulated Trigger Molecules in Polyoxymethylene Urea (PMU) microcapsules* | | | | |
| Urea | 0.2 | — | 4.8 | 1 |
| Propionic acid | — | 0.5 | 0.1 | 0.2 |
| Butyric Acid | — | — | 0.1 | 0.1 |
| Cyclic Oligosaccharide6 | 2.5 | 5 | 10 | 2.5 |
| Fragrance Oil | 10 | 12.5 | 15 | 1.5 |
| Ethanol | to 100 | to 100 | to 100 | to 100 |

| | -continued | | | |
|---|---|---|---|---|
| Deionised Water | 13.57 | 12.77 | 11.61 | 14.81 |
| Laponite7 | 2 | — | 1 | — |

*at a encapsulation efficiency of 50–85 weight %
6 Beta W7M available from Wacker-Chemie GmbH, Hanns-Seidel-Platz 4, Munchen, Germany
7 Available from Laporte Industies Ltd., Widnes, United Kingdom Examples 8–14 exemplify at least one entrapment material-compatible surfactant as a suitable release agent. Examples 15–18 exemplify suitable pH buffering materials, to raise or lower the skin pH, as a suitable release agent. Examples 19–24 exemplify an encapsulated trigger molecule, or a mixture thereof, as a suitable trigger molecule. Finally, Examples 25–28 exemplify mixtures of at least one surfactant and/or at least one pH buffering material and/or at least one encapsulated trigger molecule as mixtures of suitable destabilising materials.

The integral compositions of Examples 8–28 were prepared as follows. The destabilising material was encapsulated in the usual manner, since encapsulation is required. The Laponite, if present, is dissolved in water and then added to the composition. The entrapment material was then dissolved in ethanol at room temperature. Any suitable fragrance oil(s) (i.e., any of fragrance Examples 1–7) can be incorporated, if desired, along with the, or each, destabilising materials (pre-encapsulated) and any remaining water.

When the integral compositions of Examples 8–28 were applied to a surface, the fragrance profile of the fragrance oils remained detectable for at least 2 hours after applying the integral composition to the surface.

Refresher Compositions for use in Methods of the Present Invention—Examples 29–54

| (% wt) | 29 | 30 | 31 | 32 | 33 | 34 | 35 |
|---|---|---|---|---|---|---|---|
| Surfactants | | | | | | | |
| Silwet L-7001 | 0.1 | 0.2 | 0.3 | 0.8 | — | 1.4 | 2.8 |
| Silwet L-7002 | 0.2 | 0.2 | 0.1 | — | 1.2 | 1.4 | 2.2 |
| Fragrance Oil | 0.2 | — | — | — | — | — | — |
| Ethanol | 0 | 0 | 0 | 0 | 5 | 10 | 20 |
| Deionised Water | to 100 | to 100 | to 100 | to 100 | to 100 | to 100 | to 100 |
| Laponite | — | — | — | — | — | — | 2 |

| (% wt) | 36 | 37 | 38 | 39 |
|---|---|---|---|---|
| Non Encapsulated OR Encapsulated pHBuffers in Polyoxymethylene Urea (PMU) microcapsules* | | | | |
| Salicylic Acid | to pH 3.5 | — | — | — |
| Glycolic Acid | — | to pH 4 | — | — |
| citric acid/sodium citrate | — | — | to pH 3 | — |
| Trisodium Citrate | — | — | — | to pH 8 |
| Fragrance Oil | — | — | — | 0.2 |
| Ethanol | — | — | 10 | 20 |
| Deionised Water | to 100 | to 100 | to 100 | to 100 |
| Laponite | — | 2 | — | 1.5 |

| (% wt) | 40 | 41 | 42 | 43 | 44 | 45 |
|---|---|---|---|---|---|---|
| Non Encapsulated OR Encapsulated* Trigger Moleculess in Polyoxymethylene Urea (PMU) microcapsules | | | | | | |
| Urea | 0.2 | — | 4.8 | 1 | 2 | 0.3 |
| Propionic acid | — | 0.5 | 0.1 | 0.2 | 1 | 0.1 |
| Butyric Acid | — | — | 0.1 | 0.1 | 0.1 | 0.3 |
| Fragrance Oil | — | 0.2 | — | — | — | 0.1 |
| Ethanol | — | 5 | — | — | — | 70 |
| Deionised Water | to 100 | to 100 | to 100 | to 100 | to 100 | to 100 |
| Laponite | — | 2 | — | — | — | 1.5 |

| (% wt) | 46 | 47 | 48 | 49 |
|---|---|---|---|---|
| Surfactants | | | | |
| Silwet L-7001 | 0.1 | 0.2 | 0.3 | 0.8 |
| Silwet L-7002 | 0.2 | 0.2 | 0.1 | — |

-continued

| Non Encapsulated OR Encapsulated pH Buffers in Polyoxymethylene Urea (PMU) microcapsules* | | | | |
|---|---|---|---|---|
| Salicylic Acid | to pH 3.5 | — | — | — |
| Glycolic Acid | — | to pH 4 | — | — |
| citric acid/sodium citrate | — | — | to pH 3 | — |
| Trisodium Citrate | — | — | — | to pH 8 |
| **Non Encapsulated OR Encapsulated\* Trigger Molecules in Polyoxymethylene Urea (PMU) microcapsules** | | | | |
| Urea | 0.2 | — | 4.8 | 1 |
| Propionic acid | — | 0.5 | 0.1 | 0.2 |
| Butyric Acid | — | — | 0.1 | 0.1 |
| Fragrance Oil | — | 0.1 | 0.2 | 0.05 |
| Ethanol | — | — | 10 | 70 |
| Deionised Water | to 100 | to 100 | to 100 | to 100 |
| Laponite | 2 | — | 1 | 2 |

| (% wt) | 50 | 51 | 52 | 53 | 54 |
|---|---|---|---|---|---|
| Fragrance Oil | — | 0.1 | 0.2 | 1.0 | — |
| Ethanol | — | — | 10 | 40 | — |
| Deionised Water | to 100 | to 100 | to 100 | to 100 | to 100 |
| Laponite | 2 | — | 1 | — | — |

Examples 29–35 exemplify at least one entrapment material-compatible surfactant as a suitable release agent. Examples 36–39 exemplify suitable pH buffering materials, to raise or lower the surface pH, as a suitable release agent. Examples 40–45 exemplify an encapsulated trigger molecule, or a mixture thereof, as at least one suitable trigger molecule. Examples 46–49 exemplify mixtures of at least one surfactant and/or at least one pH buffering material and/or at least one encapsulated trigger molecule as mixtures of suitable destabilising materials. Finally, Examples 50–54 exemplify water as a suitable dissolution solvent.

The refresher compositions of Examples 29–54 were prepared as follows. The destabilising material was encapsulated in the usual manner, if encapsulation is required for a delayed release of fragrance is desired. The Laponite (if present) is dissolved in water and then added to the composition. Any suitable fragrance oil(s) (i.e., any of fragrance Examples 1–7), if present, can be incorporated, along with the, or each, destabilising material (pre-encapsulated, if required) and any water.

When refresher compositions of any of Examples 29–54 were applied to the surface to which an entrapment structure had already been applied, the fragrance profile of the fragrance oils remained detectable for at least 2 hours after applying the composition to the surface.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for improving release, on a surface, of a fragrance from an entrapment structure, of at least one fragrance oil and at least one entrapment material, the method comprising destabilising the entrapment structure by providing at least one destabilising material comprising:
   i) at least one trigger molecule which preferentially associates with one or more of the at least one entrapment material; and
   ii) at least one release agent which at least partially disrupts the entrapment structure.

2. A method according to claim 1 wherein the method comprises providing at least about 0.001%, by weight, of the destabilising material, at least about 0.001%, by weight, of the trigger molecule and at least about 0.001%, by weight, of the release agent.

3. A method according to claim 1 wherein the method comprises providing from about 0.001% to about 20%, by weight, of the trigger molecule and from about 0.001% to about 20%, by weight, of the release agent.

4. A method according to claim 1 wherein the method comprises providing from about 0.01% to about 15%, by weight, of the trigger molecule and the release agent.

5. A method according to claim 1 wherein the entrapment material is selected from the group consisting of a capsule, microcapsule, microsphere, millicapsule, starch capsule, nanocapsule and liposome.

6. A method according to claim 1 wherein the trigger molecule is selected from substituted and unsubstituted C1–C15 carboxylic acids, their salts, esters, amides, mixtures thereof, and from surfactants incompatible with said entrapment material wherein the surfactants are selected from the group consisting of nonionic, anionic, amphoteric, zwitterionic, and mixtures thereof.

7. A method according to claim 1 wherein the release agent is a dissolution solvent comprising water.

8. A method according to claim 1 wherein die release agent acts by changing the surface hydration level and is selected from pH buffering agents such as to change the pH of the surface at least one pH unit above, or below, the usual surface pH.

9. A method according to claim 8 wherein the pH buffering agents are selected from beta-hydroxy acids, alpha-hydroxy acids, sodium carbonate, sodium bicarbonate buffer systems, phosphate buffer systems, their salts, mixtures thereof; and from surfactants compatible with said entrapment material wherein the surfactants are selected from the group consisting of nonionic, anionic, amphoteric, zwitterionic, and mixtures thereof.

10. A method according to claim 9 wherein the release agent is selected from salicylic acid, glycolic acid, citric acid, their salts and mixtures thereof.

11. A method according to claim 1 wherein the destabilising material is applied to the surface after the entrapment structure is formed on the surface and wherein the destabilising material is provided in a refresher composition.

12. A method according to claim 11, wherein water comprises greater than 1%, by weight, of the refresher composition.

13. A method according to claim 11 wherein the refresher composition additionally comprises from about 0.001% to about 20%, by weight, of the fragrance oil.

14. A method according to claim 11 wherein the refresher composition additionally comprises greater than 1%, by weight, of a compatible solvent, and mixtures thereof.

15. A method according to claim 11 wherein the refresher composition further comprises a safe and effective amount of one or more of the active ingredients selected from antioxidants, antimicrobials, denaturants, dyes, hair conditioning and hair hold polymers, moisturisers, preservatives, surfactants, UV absorbers, laponite clays and mixtures thereof.

16. A method according to claim 1 wherein the destabilising material is applied to the surface while the entrapment structure is being formed thereon, the destabilising material being provided in a composition comprising:
   a) at least one fragrance oil;
   b) at least one entrapment material, wherein the fragrance oil and the entrapment material are capable, in use, of forming an entrapment structure on the surface;
   c) at least one destabilising material which permits formation of the entrapment structure on the surface but which destabilising material destabilises the entrapment structure by providing:
      i) at least one trigger molecule which preferentially associates with the entrapment material on the surface; and
      ii) at least one release agent that at least partially disrupts the entrapment structure; and
   d) at least one compatible solvent that does not interfere with formation of the entrapment structure on the surface.

17. A composition for improving release, on a surface, of a fragrance, wherein the composition comprises:
   a) at least one fragrance oil;
   b) at least one entrapment material, wherein the fragrance oil and the entrapment material are capable, in use, of forming an entrapment structure on the surface;
   c) at least one destabilising material which permits formation of the entrapment structure on the surface but which destabilising material destabilises the entrapment structure by providing:
      i) at least one trigger molecule which preferentially associates with the entrapment material on the surface; and
      ii) at least one release agent that at least partially disrupts the entrapment material; and
   d) at least one compatible solvent that does not interfere with formation of the entrapment structure on the surface.

18. A composition according to claim 17 which comprises from about 0.01% to about 99%, by weight, of the fragrance oil.

19. A composition according to claim 17 wherein the fragrance oil comprises from about 5% or greater, by weight of the fragrance oil, of a top note perfume raw material and mixtures of top note perfume raw materials wherein the top note perfume raw material has a boiling point of less than or equal to about 250° C. at 1 atmosphere pressure.

20. A composition according to claim 19 wherein the top note perfume raw material of the fragrance oil comprises 5% or greater, by weight of the top note perfume raw materials and have an odour detection threshold of less than, or equal to, 50 parts per billion.

21. A composition according to claim 17 wherein the fragrance oil comprises from about 0.01% to about 95%, by weight of the flagrance oil, of middle and base note perfume raw materials, wherein the middle and base note perfume raw materials are selected from perfume raw materials having a boiling point of greater than about 250° C. at 1 atmosphere pressure.

22. A composition according to claim 21 wherein the middle and base note perfume raw materials of the fragrance oil comprises 10% or greater, by weight of the middle and base note perfume raw materials, and have an odour detection threshold of less than, or equal to, 50 parts per billion.

23. A composition according to claim 17 wherein, within the fragrance oil, the weight ratio of top note perfume raw materials to middle or base note perfume raw materials is in the range from about 1:20 to about 20:1.

24. A composition according to claim 17 which comprises from about 0.001% to about 40%, by weight, of the entrapment material.

25. A composition according to claim 17 wherein said entrapment material is a cyclic oligosaccharide having six, seven or eight saccharide units or mixtures thereof.

26. A composition according to claim 17 wherein said entrapment material is a cyclic oligosaccharide substituted with a substituent selected from C1–C8 alkyl, hydroxyalkyl groups and mixtures thereof.

27. A composition according to claim 17 wherein said entrapment material is a cyclic oligosaccharide substituted with C1–C8 alkyl groups.

28. A composition according to claim 17 wherein said entrapment material is a cyclodextrin selected from the group consisting of α-cyclodextrin, β-cyclodextrin, methyl-α-cyclodextrin, methyl-β-cyclodextrin, hydroxypropyl-α-cyclodextrin, hydroxypropyl-β-cyclodextrin and mixtures thereof.

29. A composition according to claim 17 wherein the release agent is selected from pH buffering agents such as to change the pH of the surface at least one pH unit above, or below, the usual surface pH, and from surfactants compatible with said entrapment material wherein the surfactants are selected from the group consisting of nonionic, anionic, amphoteric, zwitterionic, and mixtures thereof.

30. A composition according to claim 17 wherein the release agent is selected from beta-hydroxy acids, alpha-hydroxy acids, mixtures thereof, sodium carbonate and sodium bicarbonate buffer systems, phosphate buffer systems, their salts, and mixtures thereof.

31. A composition according to claim 17 wherein the trigger molecule is selected from substituted or unsubstituted C1–C15 carboxylic acids, their salts, esters, amides and mixtures thereof.

32. A composition according to claim 17 which comprises at least about 0.001%, by weight, of the trigger molecule and the release agent.

33. A composition according to claim 17 wherein the trigger molecule and, optionally, the release agent is encapsulated in a capsule, microcapsule, microsphere, millicapsule, starch capsule, nanocapsule or liposome.

34. A composition according to claim 17 which comprises greater than 50%, by weight, of at least one compatible solvent.

35. A composition according to claim 17 wherein the solvent is a volatile solvent having a boiling point, at 1 atmosphere pressure, of less than about 95° C.

36. A composition according to claim 35 wherein the volatile solvent is selected from ethers, straight or branched chain alcohols and diols, volatile silicones, propellants, and mixtures thereof.

37. A composition according to claim 35 wherein the volatile solvent is ethanol.

38. A composition according to claim 17 wherein the composition further comprises a safe and effective amount of one or more of the active ingredients selected from antioxidants, antimicrobials, denaturants, dyes, hair conditioning and hair hold polymers, moisturisers, preservatives, surfactants, UV absorbers, laponite clays and mixtures thereof.

* * * * *